United States Patent

Kinsho et al.

Patent Number: 5,519,156
Date of Patent: May 21, 1996

[54] CYCLOHEXANE CARBALDEHYDE COMPOUNDS AND PROCESSES FOR PREPARING SILACYCLOHEXANE-BASED LIQUID CRYSTAL COMPOUNDS FROM THE CARBALDEHYDE

[75] Inventors: Takeshi Kinsho; Takaaki Shimizu; Tsutomu Ogihara; Tatsushi Kaneko; Mutsuo Nakashima, all of Niigata, Japan

[73] Assignee: Shin-Etsu Chemical Co., Ltd., Tokyo, Japan

[21] Appl. No.: 501,524

[22] Filed: Jul. 12, 1995

[30] Foreign Application Priority Data

Jul. 12, 1994 [JP] Japan ................ 6-182904

[51] Int. Cl.⁶ .................. C07F 7/08; C07F 7/18
[52] U.S. Cl. .................. 5 R/406; 204/157.44; 204/157.45; 204/157.64; 204/157.74
[58] Field of Search .................. 5 R/406; 204/157.44, 204/157.45, 157.64, 157.74

[56] References Cited

U.S. PATENT DOCUMENTS 4,973,732 11/1990 Cawthorn et al. .............. 556/406
5,454,977 10/1995 Shimizu et al. .............. 556/406 X

FOREIGN PATENT DOCUMENTS 0648773 4/1995 European Pat. Off. .

*Primary Examiner*—Paul F. Shaver
*Attorney, Agent, or Firm*—Lowe, Price, LeBlanc & Becker

[57] ABSTRACT

A cyclohexane carbaldehyde compound of the following formula (I)

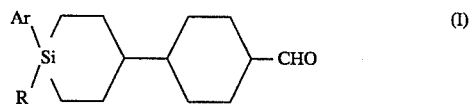

wherein Ar represents a phenyl group or a tolyl group, and R represents a phenyl group, a tolyl group, a linear alkyl group, a mono or difluoroalkyl group, a branched alkyl group or an alkoxyalkyl group. Processes for preparing a silacyclohexane-based liquid crystal compound of the following formula (II) or (III) from the cyclohexane carbaldehyde are also described

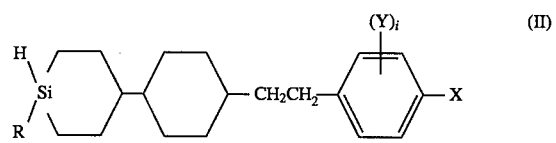

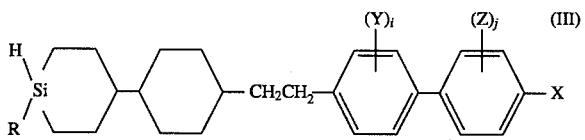

wherein R represents a phenyl group, a tolyl group, a linear alkyl group, a mono or difluoroalkyl group, a branched alkyl group or an alkoxyalkyl group, X represents R or OR, in which R has the same meaning as defined above, CN, F, Cl, Br, $CF_3$, $OCF_3$, $OCHFCl$, $OCF_2Cl$, $CF_2Cl$, $(O)_mCY_1=CX_1X_2$, $O(CH_2)_r(CF_2)_sX_3$, wherein m is a value of 0 or 1, $Y_1$ and $X_1$ independently represent H, F or Cl, $X_2$ represents F or Cl, r and s are, respectively, a value of 0, 1 or 2 provided that r+s=2, 3 or 4, and $X_3$ represents H, F or Cl, Y represents a halogen or a methyl group, Z represents a halogen or $CH_3$, i is a value of 0, 1 or 2, and j is a value of 0, 1 or 2.

14 Claims, No Drawings

CYCLOHEXANE CARBALDEHYDE COMPOUNDS AND PROCESSES FOR PREPARING SILACYCLOHEXANE-BASED LIQUID CRYSTAL COMPOUNDS FROM THE CARBALDEHYDE

BACKGROUND OF THE INVENTION

1. Field of The Invention

This invention relates to a novel cyclohexane carbaldehyde compound and also to a process for preparing a silacyclohexane-based liquid crystal compound from the carbaldehyde compound.

2. Description of the Prior Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid substances used in these liquid crystal devices depend, more or less, on the type of display, it is commonly required that the liquid crystal substances have a wide range of liquid crystal working temperatures and that they be stable against moisture, air, light, heat, electric field and the like. Moreover, the liquid crystal substances should desirably be low in viscosity and should ensure a short address time, a low threshold voltage and a high contrast in a cell.

As the liquid crystal display devices have wider utility in recent years, the characteristic properties required for liquid Crystal materials become much severer. In addition, those characteristics which have never been required for conventional liquid crystal substances are now expected such as a lower drive voltage, a wider working temperature range which could satisfy the needs for on-vehicle materials and an improvement in low temperature performance.

Under these circumstances, we developed novel silacyclohexane-based liquid crystal compounds which contain a silicon atom in the molecule so that the characteristic properties for use as a liquid crystal substance are improved. These liquid crystal compounds have been proposed in co-pending U.S. application Ser. Nos. 08/377961, filed Jan. 25, 1995 and 08/395706, filed Feb. 28, 1995 (corresponding to European Patent Application Nos. 95101167.5, filed Jan. 27, 1995 and 951029.8.1, filed Mar. 1, 1995 and Korean Patent Application Nos. 95-1701, filed Jan. 28, 1995 and 95-4084, filed Feb. 28, 1995, respectively).

SUMMARY OF THE INVENTION

It is an object of the invention to provide a cyclohexane carbaldehyde compound which is a useful intermediate for preparing silacyclohexane-based liquid crystal compounds.

It is another object of the invention to provide processes for preparing silacyclohexane-based liquid crystal compounds which are kinds of derivatives of the cyclohexane carbaldehyde compound.

The above objects can be achieved, according to one embodiment of the invention, by a cyclohexane carbaldehyde compound of the following formula (I)

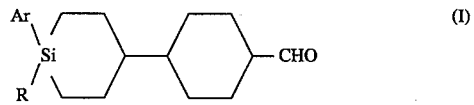

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms.

The cyclohexane carbaldehyde compound of the above formula (I) is useful as an intermediate for preparing a silacyclohexane-based liquid compound of the following general formula (II)

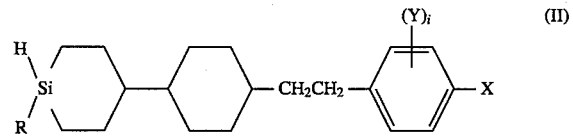

wherein R has the same meaning as defined above and represents a phenyl group, a tolyl group, a linear alkyl group having from I to 10 carbon atoms, a mono or difiuoroalkyl group having from 1 to 10 carbon atoms, a branched alkyl group having from 3 to 8 carbon atoms or an alkoxyalkyl group having from 2 to 7 carbon atoms, X represents R or OR, in which R has the same meaning as defined above, CN, F, Cl, Br, $CF_3$, $OCF_3$, $OCHF_2$, $OCHFCl$, $OCF_2Cl$, $CF_2Cl$, $(O)_mCY_1=CX_1X_2$, or $O(CH_2)_r(CF_2)_sX_3$ wherein m is a value of 0 or 1, $Y_1$ and $X_1$ independently represent H, F or Cl, $X_2$ represents F or Cl, r and s are, respectively, a value of 0, 1 or 2 provided that r+s=2, 3 or 4, and $X_3$ represents H, F or Cl, Y represents a halogen, preferably Cl or F, or a methyl group, i is a value of 0, 1 or 2, or a silacyclohexane-based liquid crystal compound of the following general formula (III)

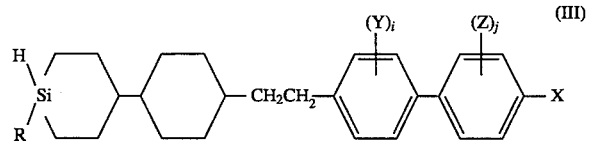

wherein R, Y, X and i have, respectively, the same meanings as defined with respect to the formula (II), Z represents a halogen or a methyl group, and i is zero or an integer of 1 or 2.

The silacyclohexane-based liquid crystal compound of the general formula (II) is prepared according to a process of the invention which comprises:

subjecting the cyclohexane carbaldehyde of the general formula (I) to reaction with a ylide compound of the following general formula (1)

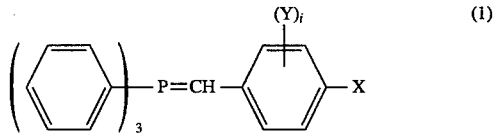

wherein X has the same meaning as defined with respect to the formula (II) and represents R or OR, in which R has the same meaning as defined hereinbefore, CN, F, Cl, Br, $CF_3$, $OCF_3$, $OCHF_2$, $OCHFCl$, $OCF_2Cl$, $CF_2Cl$, $(O)_mCY_1=$ $CX_1X_2$, or $O(CH_2)_r(CF_2)_sX_3$ wherein m is a value of 0 or 1, $Y_1$ and $X_1$ independently represent H, F or Cl, $X_2$ represents F or Cl, r and s are, respectively, a value of 0, 1 or 2 provided that r+s=2, 3 or 4, and $X_3$ represents H, F or Cl, Y represents a halogen, preferably Cl or F, or a methyl group, i is a value of 0, 1 or 2, thereby obtaining a compound of the following formula (2)

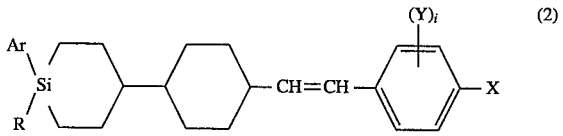

subjecting the thus obtained compound of the formula (2) to hydrogenation to obtain a compound of the following general formula (3)

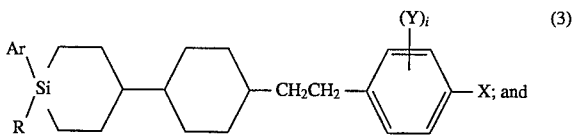

further subjecting the compound of the formula (3) to de-silylation and then to reduction to obtain a compound of the general formula (II)

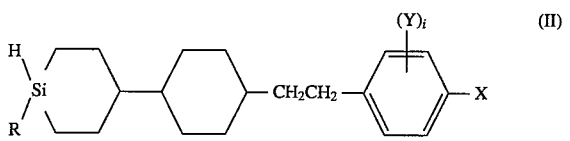

In the above formulas (2) to (3), Ar, R, Y, X and i have, respectively, the same meanings as defined hereinbefore.

Moreover, the silacyclohexne-based liquid crystal compound of the general formula (III) can be prepped by a process which comprises:

subjecting a cyclohexane carbaldehyde compound of the afore-indicated general formula (I) with a ylide compound of the following general formula (4)

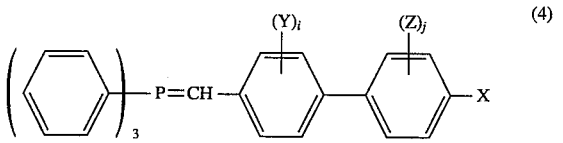

wherein X represents R or OR, in which R has the same meaning as defined before, CN, F, Cl, Br, $CF_3$, $OCF_3$, $OCHF_2$, $OCHFCl$, $OCF_2Cl$, $CF_2Cl$, $(O)_mCY_1=CX_1X_2$, or $O(CH_2)_r(CF_2)_sX_3$ wherein m is a value of 0 or 1, $Y_1$ and $X_1$ independently represent H, F or Cl, $X_2$ represents F or Cl, r and s are, respectively, a value of 0, 1 or 2 provided that r+s=2, 3 or 4, or $X_3$ represents H, F or Cl, Y and Z independently represent a halogen, preferably F or Cl, or a methyl group, i and j are independently a value of 0, 1 or 2, thereby obtaining a compound of the following general formula (5)

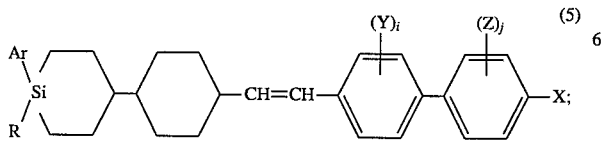

subjecting the compound of the formula (5) to hydrogenation to obtain a compound of the following general formula (6)

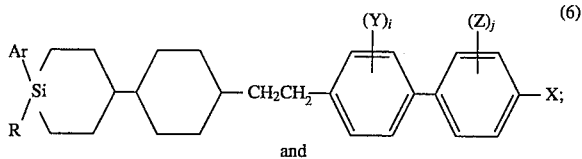

and further subjecting the thus obtained compound of the formula (6) to desilylation and then to reduction to obtain a silacyclohexane-based compound of the general formula (III)

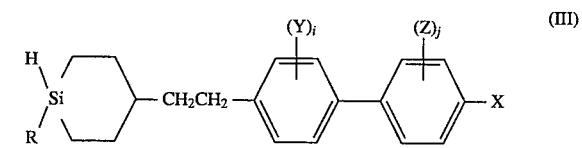

In these general formulas including the formulas (5), (6) and (III), Ar, R, X, Y, Z, i and j have, respectively, the same meanings as defined hereinbefore and whenever appearing hereinafter and may not be again defined in some cases.

Alternatively, the silacyclohexane-based liquid crystal compound of the general formula (III) may also be prepared according to a process which comprises:

reacting a cyclohexane carbaldehyde of the More-indicated general formula (I) with a ylide compound of the following general formula (7)

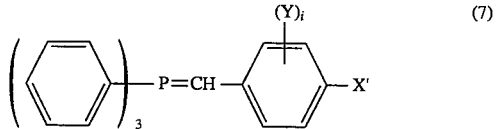

wherein X' represents a halogen, preferably Cl, Br or I, Y has the same meaning as defined hereinbefore and represents a halogen or a methyl group, and i is a value of 0, 1 or 2, thereby obtaining a compound of the following general formula (8)

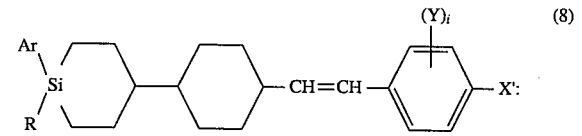

further subjecting the compound of the formula (8) to reaction with an organometal compound of the following general formula (9) in the presence of a catalyst of a transition metal compound

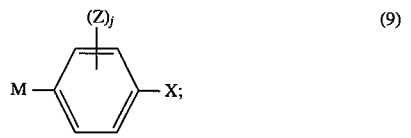

wherein X has the same meaning as defined with respect to the formula (II), M represents MgU or ZnU wherein U represents a halogen, preferably Cl, Br or I, $TiU_k(OW)_{3-k}$ wherein U has the same meaning as defined above, W represents an alkyl group, preferably having from 1 to 6 carbon atoms, and k is a value of 0, 1, 2 or 3, or $B(OV)_2$ wherein V represents a hydrogen atom or an alkyl group, preferably having from 1 to 4 carbon atoms, and Z has the same meaning as defined hereinbefore, thereby obtaining a compound of the following general formula (10)

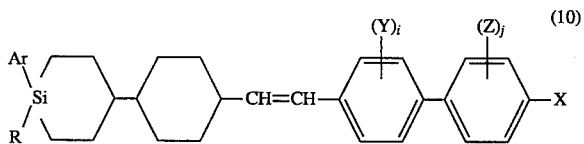

subjecting the compound of the formula (10) to hydrogenation

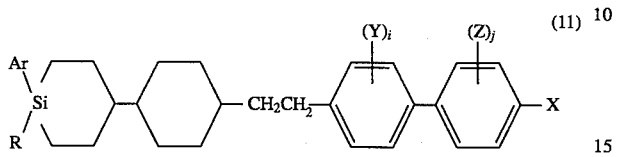

further subjecting the compound of the formula (11) to de-silylation and then to reduction to obtain a silacyclohexane-based liquid crystal compound of the following general formula (III)

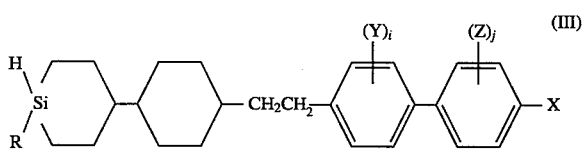

DETAILED DESCRIPTION OF THE INVENTION

The embodiments of the invention are described. It will be noted that Ar, R, X, X', Y, Z, i, and j which have, respectively, been defined in the foregoing formulas have, respectively, the same meanings as defined before and may not be sometimes defined again in such formulas appearing hereinafter. According to one embodiment of the invention, there is provided a cyclohexane carbaldehyde compound of the following general formula (I)

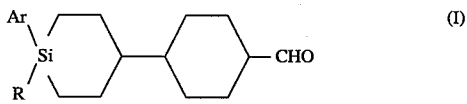

wherein Ar represents a phenyl group or a tolyl group, R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms.

Examples of the linear alkyl group having from 1 to 10 carbon represented by R in the formula (I) include methyl, ethyl, n-propyl, n-butyl, n-pentyl, n-hexyl, n-heptyl, n-octyl, n-nonyl and n-decyl. Examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1fluoroheptyl, 1-fluorooctyl, 1-fluorononyl, 1-fluorodecyl, 2-fluoroethyl, 2-fluoropropyl, 2-fluorobutyl, 2-fluoropentyl, 2fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Examples of the branched alkyl group having 3 to 8 carbon atoms include iso-propyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl.

Of these, preferred linear alkyl groups are ones having from 3 to 7 carbon atoms and include, for example, n-propyl, n-butyl, n-pentyl, n-hexyl and n-heptyl. Likewise, preferred mono or difluoroalkyl groups include 2-fluoroethyl, 2-fluoropropyl, 2-fluorobutyl, 2-fluoropentyl, 2-fluorohexyl, 2-fluoroheptyl, 4fluorobutyl, 4-fluoropentyl, 4-fluorohexyl, 4-fluoroheptyl, 5-fluoroheptyl, 6fluorohexyl, 7-fluoroheptyl, 2,2-difluoroethyl, 2,2-difluoropropyl, 2,2difluorobutyl, 2,2-difluoropentyl, 2,2-difluorohexyl, 2,2-difluoroheptyl, 4,4difluorobutyl, 4,4-difluoropentyl, 4,4-difluorohexyl, 4,4-difluoroheptyl, 5,5difluoropentyl, 5,5-difluorohexyl, 5,5-difluoroheptyl, 6,6-difluorohexyl, 6,6difluoroheptyl and 7,7-difluoroheptyl.

Preferred branched alkyl groups include, for example, isopropyl, 1methylpentyl, 2-methylpentyl, 1-methylbutyl, 2-methylbutyl, 3-methylbutyl, 1methylpentyl and 2-ethylhexyl.

Preferred alkoxyalkyl groups include methoxymethyl, methoxyethyl, methoxypropyl, methoxypentyl, ethoxymethyl, ethoxyethyl, propoxymethyl and pentoxymethyl.

The compound of the general formula (I) is prepared from a cyclohexanone compound which we proposed in Japanese Patent Application No. 6-71825, filed Mar. 24, 1994 and not yet laid open.

For instance, according to the following reaction sequence (12), a ylide compound obtained from an alkoxymethyltriphenylphosphonium salt by the action of a base and the cyclohexane compound are subjected to the Wittig reaction to obtain an alkyl enol ether, followed by hydrolysis with an acid catalyst to obtain the cyclohexane carbaldehyde of the formula (I)

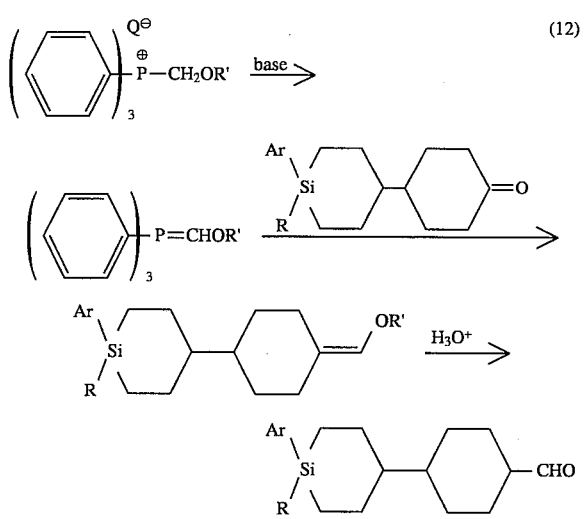
(12)

wherein R' represents an alkyl group having from 1 to 10 carbon atoms, preferably from 1 to 4 carbon atoms, and Q represents a halogen, preferably including Cl, Br or I.

Examples of the alkoxymethyltriphenylphosphonium salt used in the above reaction sequence include methoxymethyltriphenylphosphonium chloride, methoxymethyltriphenylphosphonium bromide, methoxymethyltriphenylphosphonium iodide, ethoxymethyltriphenylphosphonium chloride, ethoxymethyltriphenylphosphonium bromide, ethoxymethyltriphenylphosphonium iodide and the like.

The bases used for the formation of the ylide compound include organolithium compounds such as n-butyllithium, s-butyllithium, t-butyllithium, methyllithium, phenyllithium and the like, alkoxides such as sodium methoxide, sodium ethoxide, potassium t-butoxide and the like, and dimsyl sodium.

The reaction is usually effected in solvents inert to the reaction system. examples of the solvent include ethers such as tetrahydrofuran, diethyl ether, di-n-butyl ether, 1,4-dioxane and the like or mixed solvents of the ethers with hydrocarbons such as n-hexane, n-heptane, iso-octane, benzene, toluene, xylene, cumene and the like or aprotic polar solvents such as N,N-dimethylformamide, dimethylsulfoxide, hexamethylphosphoric triamide and the like. This reaction is preferably effected at a temperature of from 0° C. to the refluxing temperature of a solvent used, more preferably from 10° to 40° C.

The cyclohexanone compound is then added to the resultant ylide compound formed in the solvent to cause the Wtrig reaction to proceed thereby obtaining an alkyl enol ether compound.

The alkyl enol ether compound is hydrolyzed in the presence of an acid catalyst. Examples of the acid include inorganic acids such as hydrochloric acid, sulfuric acid and the like, and organic acids such as acetic acid, oxalic acid, trifluoroacefic acid, chloroacetic acid and the like. The hydrolysis is effected at a temperature of from 0° to 80° C., preferably from 10° to 40° C.

In view of economy, these reactions are optimally carried out at normal temperatures without resorting to any specific techniques and apparatus.

The thus obtained cyclohexane carbaldehyde compounds may be used for the preparation of various types of silacyclohexaneobased liquid crystal compounds. The processes for preparing derivatives of the cyclohexane carbaldehyde compounds are then described.

It should be noted that the preparation of the liquid crystal compounds may be performed under relatively wide temperature and time conditions as in the case of the preparation of the carbaldehyde compounds and that the reaction conditions as will be set out in the respective steps are not for limitation. Most steps favorably proceed at normal temperatures and normal pressures although higher temperatures and/or higher pressures may be used if a higher reaction velocity is required. In this sense, the reaction conditions including the reaction temperature substantially in all the steps should not be taken as critical.

First, when phosphorus ylide compounds which are readily prepared from a corresponding phosphonium salt by the action of bases are reacted with the cyclohexane carbaldehyde compounds according to the following reaction sequence (13), olefinic compounds are obtained through the Wittig reaction

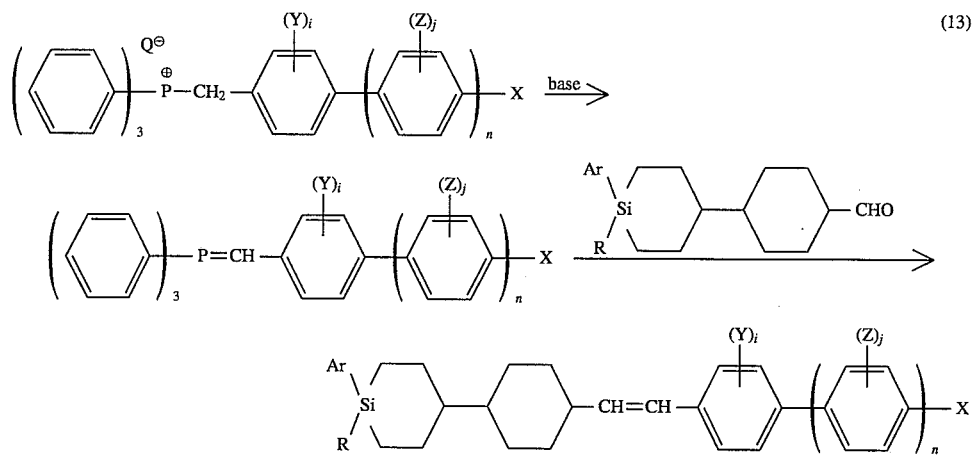
(13)

wherein Q, Y, Z, X, Ar, R, i and i have, respectively, the same meanings as defined hereinbefore and n is a value of 0 or 1.

The bases useful for the formation of the ylides include organolithium compounds such as n-butyllithium, s-butyllithium, t-butyllithium, methyllithium, phenyllithium and the like, alkoxides such as sodium methoxide, sodium ethoxide, potassium t-butoxide and the like, and dimsyl sodium.

The reactions are effected in solvents including ethers such as tetrahydrofuran, diethyl ether, di-n-butyl ether, 1,4-dioxane and the like, or mixtures of the ethers with aprotic polar solvents including hydrocarbons such as n-hexane, n-heptane, iso-octane, benzene, toluene, xylene, cumene and the like, and aprotic polar solvents such as N,N-dimethylformamide, dimethylsulfoxide, hexamethylphosphoric triamide and the like. These reactions are effected preferably at a temperature of from 0° C. to the refluxing temperature of the solvent used, more preferably from 10° to 40° C.

The cyclohexane carbaldehyde compound is then added to the thus obtained ylide compound formed in the solvent, whereupon the Wittig reaction is caused to proceed to obtain an olefinic compound.

Next, the thus obtained olefinic compound is subjected to catalytic reduction thereby hydrogenating the double bond thereof to obtain a saturated compound.

The hydrogenation reaction is carried out by a usual manner. Preferably, the hydrogenation is effected at a temperature ranging from 0° to 150° C., more preferably from 20° to 100° C. A higher pressure of hydrogen results in a higher reaction velocity. In view of limitation on the type of reactor, it is preferred to use a hydrogen pressure ranging from an atmospheric pressure to 20 kg/cm$^2$.

This catalytic reduction proceeds according to the following reaction formula (14)

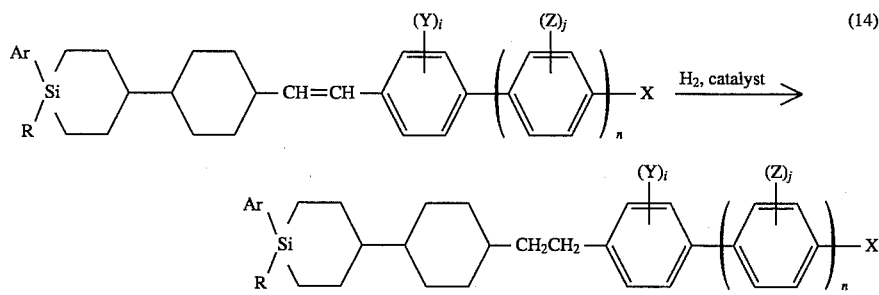

The catalysts used for the hydrogenation include, for example, metals such as palladium, platinum, rhodium, nickel, ruthenium and the like, metal oxides or combinations of metals and supports. Preferably, there are used palladium-carbon, palladium-barium sulfate, palladium-diatomaceous earth, platinum oxide, platinum-carbon, rhodium-carbon, Raney nickel, palladium oxide, nickel-diatomaceous earth, and the like. More preferably, Pa (palladium) and Ni (nickel)-based catalysts are used.

Thereafter, the saturated compound is subjected to desilylation reaction with an electrophilic reagent to obtain a halosilacyclohexane compound, followed by reduction reaction as shown in the following reaction sequence (15)

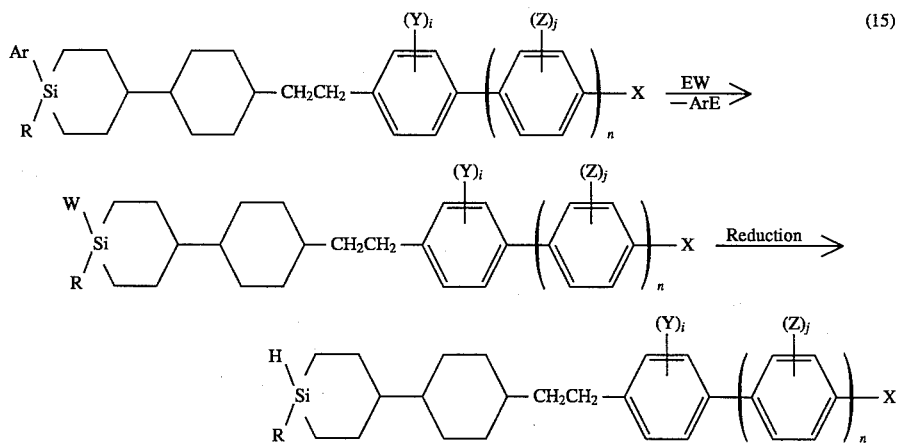

wherein EW is an electrophilic reagent in which W represents a halogen.

The electrophilic reagents include halogens, hydrogen halides, metal halides, sulfonic derivatives, acid halides, alkyl halides and the like. Preferably, there are mentioned bromine, iodine, chlorine, iodine monochloride, hydrogen chloride, hydrogen bromide, hydrogen iodide, mercury (II) chloride, trimethylsilyl chlorosulfonate, acetyl chloride, acetyl bromide, benzoyl chloride, t-butyl chloride and the like. In order to increase the reaction velocity, Lewis acids such as aluminium chloride, zinc chloride, titanium tetrachloride, boron trifluofide and the like may be added to the reaction system. Alternatively, the reaction system may be irradiated with actinic light such as ultraviolet rays and/or visible rays.

Preferably, the de-silylation reaction using the electrophilic agent is carried out at a temperature of from 0° to 80° C., more preferably from 10° to 40° C.

The reagents used for the reduction of the halosilacyclohexane compound include metal hydrides such as sodium hydride, calcium hydride, trialkylsilanes, boranes, dialkylaluminium compounds and the like, complex hydrides such as lithium aluminohydride (i.e. lithium aluminium hydride), sodium borohydride, lithium borohydride, potassium borohydride, tributylammonium borohydride and the like, and substituted hydrides thereof such as lithium trialkoxyaluminium hydrides, sodium di(methoxyethoxy)aluminium hydride, lithium triethylborohydride, sodium cyanoborohydride and the like.

Although not limitative, the reduction of the halosilacyclohexane is carried out preferably at a temperature of from 0° to 150° C., more preferably from 20° to 120° C.

By the above process, the silacyclohexane-based liquid crystal compounds can be prepared.

Among the compounds obtained in the reaction formula (13), a compound of the following formula (16) corresponding to a compound of the formula (13) where n=0, can be converted to a compound of the following general formula (17)

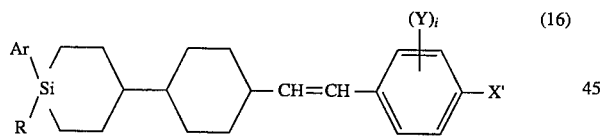
(16)

wherein Ar, R, Y and i have, respectively, the same meanings as defined hereinbefore and X' represents a halogen, preferably including Cl, Br or I,

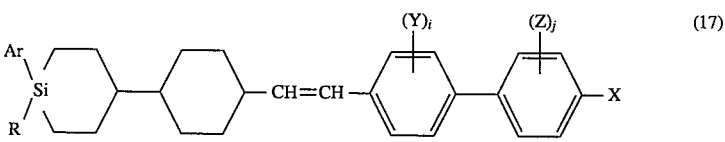
(17)

The above reaction is carried out according to the following reaction formula (18)

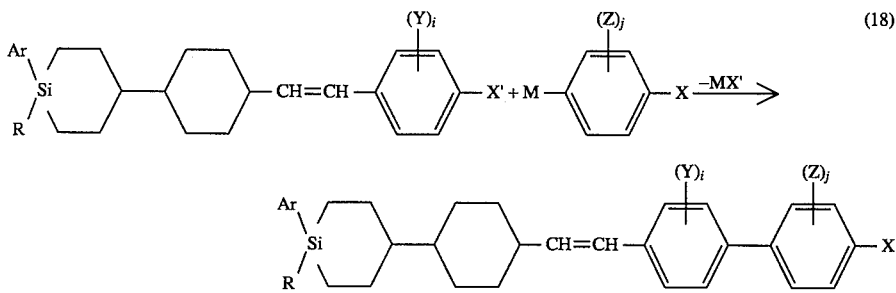

wherein M represents MgU or ZnU wherein U represents a halogen preferably including Cl, Br or I, $TiU_k(OW)_{3-k}$ wherein U has the same meaning as defined above, W represents an alkyl group having preferably from 1 to 6 carbon atoms and k is a value of 0, 1, 2 or 3, or $B(OV_2)$ wherein V represents a hydrogen atom or an alkyl group having preferably from 1 to 4 carbon atoms. In the above formula (18), X has the same meaning as defined hereinbefore.

This reaction is effected in the presence of a catalyst of a transition metal compound. Preferred examples of the catalyst include palladium or nickel compounds. The palladium catalysts include, for example, zero valent palladium compounds such as tetrakis(triphenylphosphine)palladium (0), di-[1,2-bis(diphenylphosphino)ethane]palladium (0) and the like, compounds consisting of divalent palladium compounds, such as palladium acetate, palladium chloride, [1,1'-bis(diphenylphosphino)ferrocene]palladium (II) chloride and the like, and combinations of those compounds mentioned above with reducing agents.

Examples of the nickel catalyst include divalent nickel compounds such as [1,3-bis (diphenylphosphino)propane] nickel (II) chloride, [1,2-bis(diphenylphosphino)ethane] nickel (II) chloride, bis(triphenylphosphine) nickel (II) chloride and the like, zero valent nickel compounds such as tetrakis(triphenylphosphine) nickel (0) and the like.

If the organometallic compound used as one of the reactants is a boric acid derivative of the formula (18) wherein M represents $B(OV)_2$, it is preferred that the reaction is carried out in the presence of a base. Examples of the base include inorganic bases such as sodium carbonate, sodium hydrogencarbonate, potassium carbonate, sodium hydroxide, potassium hydroxide and the like, and organic bases such as triethylamine, tributylamine, dimethylaniline and the like.

Preferably, the reaction is carried out at a temperature ranging from 0° to 100° C., more preferably from 20° to 70° C.

The compound obtained according to the reaction formula (18) can be converted into a silacyclohexane-based liquid crystal compound according to the reaction sequences (14) and (15) indicated before.

The thus prepared compounds may be purified by a usual manner such as recrystallization, chromatography or the like, thereby obtaining silacyclohexane-based liquid crystal compounds in an intended trans, trans form, if necessary.

The present invention is more particularly described by way of examples wherein unless otherwise indicated, the reactions were effected at room temperature which was set at 25° C.

EXAMPLE 1

Preparation of 4-(4-phenyl-4-n-propyl-4-silacyclohexyl)cyclohexane carbaldehyde 11.3 g of potassium t-butoxide was added to a mixture of 35 g of methoxymethyltriphenylphosphonium chloride and 300 ml of tetrahydrofuran at 0° C. to prepare a ylide solution. 31.5 g of (4-phenyl-4-n-propyl-4-silacyclohexyl-)cyclohexanone was dropped in the ylide solution. After agitation at room temperature for 2 hours, the reaction mixture was poured into water, followed by extraction with ethyl acetate and then by washing with brine, drying and concentration to obtain a residue. noHexane was added to the residue and the resultant crystals of triphenylphosphine oxide were removed by filtration. The resultant tiltrate was concentrated to obtain a corresponding methyl enol ether, followed by addition of 180 ml of methylene chloride and 200 ml of 20% hydrochloric acid and agitation at room temperature for 18 hours. The methylene chloride phase or solution was collected, and washed with brine, dried and concentrated, followed by purification through column chromatography to obtain 31.2 g (yield: 95%) of the intended product. The results of IR and NMR analyses are shown below.

IR (liquid film) $v_{max}$: 2920, 2860, 1720, 1440, 1195, 1110 $cm^{31\ 1}$ $^1$H-NMR (100 MHz, $CDCl_3$)δ:0.50–2.52 (25H, m), 7.20–7.65 (5H, m), 9.50–9.76 (1H, d×2 (a signal corresponding to 1H by combining two doublets corresponding to steric isomers)

EXAMPLE 2

Preparation of 4-(4-phenyl-4-n-pentyl-4-silacyclohexyl)cyclohexane carbaldehyde

The general procedure of Example I was repeated using (4-phenyl-4-n-pentyl- 4-silacyclohexyl)cyclohexanone, thereby obtaining 4-(4-phenyl-4-n-pentyl- 4-silacyclohexyl)cyclohexane carbaldehyde with the following results of IR and $^1$H-NMR analyses.

IR (liquid film) $v_{max}$: 2920, 2860, 1720, 1445, 1190, 1100 $cm^{-1}$ $^1$H-NMR (100 MHz, $CDCl_3$)δ:0.50–2.50 (29H, m), 7.20–7.65 (5H, m), 9.50–9.76 (1H, d×2) ppm

EXAMPLE 3

Preparation of 4-(4,4-diphenyl-4-silacyclohexyl)cyclohexane carbaldehyde

The general procedure of Example 1 was repeated using (4,4-diphenyl-4-silacyclohexyl)cyclohexanone, thereby obtaining 4-(4,4-diphenyl-4-silacyclohexyl)cyclohexane carbaldehyde with the following results of a melting point and IR and $^1$H-NMR analyses.

Melting point: 107° C.

IR (KBr disc) $v_{vmax}$: 2920, 2850, 1715, 1425, 1115, 1105 cm$^{-1}$ $^1$H-NMR (CDC$_3$)δ: 0.80–2.50 (19H, m), 7.20–7.75 (10H, m), 9.50–9.70 (1H, m) ppm

EXAMPLE 4

Preparation of trans-4-(trans-4-(2-(3,4-difiuorophenyl)ethyl)cyclohexyl)-1-n-propyl-1-silacyclohexane 12.0 g of potassium t-butoxide was added to a mixture of 48.0 g of 3,4-difiuorobenzyltriphenylphosphonium bromide and 400 ml of tetrahydrofuran to obtain a ylide solution. 32.9 g of 4-(4-phenyl-4-n-propyl-4-silacyclohexyl)cyclohexane carbaldehyde was dropped in the solution. After agitation at room temperature for 2 hours, the reaction mixture was charged into water and extracted with ethyl acetate. The ethyl acetate phase or solution was subjected to washing with brine, drying and concentration to obtain a residue, to which n-hexane was added. The resultant crystals of triphenylphosphine oxide were removed by filtration and the flitrate was concentrated. The resultant residue was purified through column chromatography to obtain 39.9 g (yield: 91%) of 4-(4-(2-(3,4-difluorophenyl)ethenyl)cyclohexyl)-1-phenyl-1-n-propyl-1-silacyclohexane.

The results of IR analysis are as follows.

IR (liquid film) $v_{max}$: 2920, 2860, 1515, 1290, 1100, 960 cm$^{-1}$ 38.0 g of the thus obtained product was dissolved in 300 ml of ethyl acetate, followed by catalytic reduction in the presence of 500 mg of palladiumcarbon used as a catalyst. After absorption of one equivalent of hydrogen, the catalyst was removed by filtration and the resultant flitrate was concentrated to obtain 38.2 g (quantitative yield) of 4-(4-(2-(3,4-difluorophenyl)ethyl)cyclohexyl)-1-phenyl-1-n-propyl-1-silacyclohexane. The results of IR analysis of the product are shown below.

IR (liquid film) $v_{max}$: 2920, 2860, 1515, 1280, 1110 cm$^{-1}$ 13.0 g of iodine monochloride was dropped in a mixture of 30.0 g (68 mmols) of the thus obtained product and 500 ml of carbon tetrachloride, followed by agitation at room temperature for 30 minutes. The mixture was concentrated to obtain a crude product of 1-chloro-4-(2-(3,4-difluorophenyl)ethyl)cyclohexyl-1-phenyl-1-silacyclohexane. This product was dissolved in 30 ml of tetrahydrofuran, which was dropped in a mixture of 2.00 g of lithium aluminium hydride and 20 ml of tetrahydrofuran, followed by agitation at 40° C. for 12 hours. The reaction mixture was charged into diluted hydrochloric acid and extracted with ethyl acetate. The resultant ethyl acetate solution was washed with brine, dried and concentrated, followed by purification through column chromatography to obtain 12.8 g of the intended product (yield: 52%). The results of IR and NMR analyses are shown below.

IR (liquid film) $v_{max}$: 2920, 2852, 2100, 1520, 1286, 887, 818 cm$^{-1}$ $^{13}$C-NMR (CDCl$_3$) δ: 10.14 (s),14.79 (s), 17.79 (s), 17.95 (s), 28.61 (s), 29.58 (s), 32.54 (s), 33.54 (s), 37.46 (s), 39.08 9s), 44.16 (s), 45.96 (s), 116.66 (d), 116.92 (d), 123.93 (dd), 140.06 (dd), 147.50 (dd), 151.1`2 (dd) ppm

EXAMPLE 5

Preparation of trans-4-(trans-4-(2-(4-fiuorophenyl)ethyl)cyclohexyl)-1-n-propyl-1-silacyclohexane The general procedure of Example 4 was repeated using 4fiuorobenzyltriphenylphosphonium bromide, thereby obtaining trans-4-(trans- 4(2-(4-fiuorophenyl)ethyl)cyclohexyl)-1-n-propyl-1-silacyclohexane with the following results of IR and $^{13}$C-NMR analyses.

IR (KBr) $v_{max}$: 2918, 2850, 2100, 1512, 1232, 887, 823 cm$^{-1}$ $^{13}$C-NMR (CDCl$_3$ ): 10.12 (s), 14.79 (s), 17.80 (s), 17.94 (s), 28.60 (s), 29.60 (s), 32.51 (s), 33.58 (s), 37.47 (s), 39.45 (s), 44.15 (s), 45.96 (s), 114.90 (d), 129.54 (d), 138.73 (d), 161.07 (d)ppm

EXAMPLE 6

Preparation of trans-4-(trans-4-(2-(4-fiuorophenyl)ethyl)cyclohexyl)-1-n-pentyl-1-silacyclohexane The general procedure of Example 4 was repeated using 4-fluorobenzyltriphenylphosphonium bromide and 4-(4-phenyl-4-n-pentyl-4-silacyclohexyl)cyclohexane carbaldehyde, thereby obtaining trans-4-(trans-4-( 2-(4-fiuorophenyl)ethyl)cyclohexyl)- 1-n-pentyl-1-silacyclohexane with the following results of IR and $^{13}$C-NMR analyses.

IR (KBr, disc) $v_{max}$: 2918, 2850, 2100, 1512, 1230, 887, 823 cm$^{-1}$ $^{13}$C-NMR (CDCl$_3$): 10.11 (s), 12.19 (s), 14.00 (s), 22.36 (s), 24.12 (s), 28.60 (s), 29.62 (s), 32.52 (s), 33.59 (s), 35.40 (s), 37.48 (s), 39.47 (s), 44.16 (s), 45.96 (s), 114.9 (d), 129.54 (d), 138.73 (d), 161.08 (d) ppm

EXAMPLE 7

Preparation of trans-4-(transo4-(2-(3,4-difiuorophenyl)ethyl)cyclohexyl)-1-n-pentyl-1-silacyclohexane The general procedure of Example 4 was repeated using 4-(4-phenyl-4-n-pentyl- 4-silacyclohexyl)cyclohexane carbaldehyde, thereby obtaining trans-4-(trans- 4-(2-(3,4-difiuorophenyl)ethyl)cyclohexyl)-1-n-pentyl-1-silacyclohexane with the following results of IR and $^{13}$C-NMR analyses.

IR (KBr) $v_{max}$: 2920, 2852, 2098, 1520, 1286, 1211, 1119, 887, 816 cm$^{-1}$ $^{13}$C-NMR (CDCl$_3$): 10.10 (s), 10.46 (s), 12.19 (s), 13.99 (s), 22.36 (s), 24.11 (s), 28.60 (s), 29.57 (s), 32.54 (s), 33.54 (s), 35.40 (s), 37.41 (s), 39.06 (s), 44.12 (s), 45.94 (s), 116.71 (d), 116.95 (d), 123.96 (dd), 140.09 (dd), 147.50 (dd), 151.13 (dd) ppm

EXAMPLE 8

Preparation of trans-4-(trans-4-(2-(4-trifiuoromethoxyphenyl)ethyl)cyclohexyl)-1-n-propyl-1-silacyclohexane The general procedure of Example 4 was repeated using 4-trifluoromethoxybenzyltriphenylphosphonium bromide, thereby obtaining trans-4-(trans-4-(2-(4-trifiuoromethoxyphenyl)ethyl)cyclohexyl)-1-n-propyl-1-silacyclohexane with the following results of IR and $^{13}$C-NMR analyses.

IR (KBr, disc) $v_{max}$: 2918, 2848, 2102, 1510, 1279, 1211, 1198, 1165, 887, 818 cm$^{-1}$ $^{13}$C-NMR (CDCl$_3$): 10.16 (s), 14.82 (s), 17.79 (s), 17.97 (s), 28.65 (s), 29.63 (s), 32.73 (s), 33.60 (s), 37.60 (s), 39.29 (s), 44.21 (s), 46.02 (s), 120.58 (q), 120.81 (s), 129.45 (s), 141.92 (s), 147.2 (q)ppm

EXAMPLE 9

Preparation of trans-4-(trans-4-(2-(4-trifluoromethoxyphenyl)ethyl)cyclohexyl)-1-n-pentyl-1-silacyclohexane The general procedure of Example 4 was repeated using 4-trifluoromethoxybenzyltriphenylphosphonium bromide and 4-(4-phenyl-4-n-pentyl- 4-silacyclohexyl)cyclohexane carbaldehyde, thereby obtaining trans-4-(trans- 4-(2-(4-trifluoromethoxyphenyl)ethyl)cyclohexyl)-1-n-pentyl-1-silacyclohexane with the following results of IR and $^{13}$C-NMR analyses.

IR (KBr, disc) $v_{max}$: 2920, 2850, 2102, 1510, 1223, 1198, 1165, 887, 833, 816 cm$^{-1}$ $^{13}$C-NMR (CDCl$_3$): 10.12 (s), 12.20 (s), 13.99 (s), 22.37 (s), 24.13 (s), 28.62 (s), 29.62 (s), 32.70 (s), 33.58 (s), 35.41 (s), 37.56 (s), 39.28 (s), 44.17 (s), 45.99 (s), 120.56 (q), 120.81 (s), 129.46 (s), 141.92 (s), 147.19 (q) ppm

EXAMPLE 10

Preparation of trans-4-(trans-4-(2-(4-(4-chlorophenyl)phenyl)ethyl)cyclohexyl)- 1-n-propyl-1-silacyclohexane The general procedure of Example 4 was repeated using 4-chlorobenzyltriphenylphosphonium bromide, thereby obtaining trans-4-(trans- 4-(2-(4-(4-chlorophenyl)phenyl)ethyl)cyclohexyl)-1-n-propyl- 1-silacyclohexane with the following results of IR and $^{13}$C-NMR analyses.

IR (KBr, disc) $v_{max}$: 2918, 2848, 2100, 1487, 1095, 1003, 887, 843, 810 cm$^{-1}$ $^{13}$C-NMR (CDCl$_3$): 10.12 (s), 14.79 (s), 17.81 (s), 17.94 (s), 28.60 (s), 29.61 (s), 32.97 (s), 33.60 (s), 37.58 (s), 39.31 (s), 44.16 (s), 45.96 (s), 126.80 (s), 128.17 (s), 128.81 (s), 128.86 (s), 132.98 (s), 137.20 (s), 139.60 (s), 142.80 (s) ppm

EXAMPLE 11

Preparation of trans-4-(trans-4-(2-(4-(4-chloro-3-fluorophenyl)phenyl)ethyl)cyclohexyl)-1-n-propyl-1-silacyclohexane The general procedure of Example 4 was repeated using 4-chloro-3-fluorobenzyltriphenylphosphonium bromide, thereby obtaining trans-4-(trans- 4-(2-(4-(4-chloro-3-fluorophenyl)phenyl)ethyl)cyclohexyl)-1-n-propyl-1-silacyclohexane with the following results of IR and $^{13}$C-NMR analyses.

IR (KBr, disc) $v_{max}$: 2920, 2850, 2096, 1560, 1481, 1200, 1070, 982, 889, 845, 804 cm$^{-1}$ $^{13}$C-NMR (CDCl$_3$): 10.12 (s), 14.79 (s), 17.79 (s), 17.93 (s), 28.60 (s), 29.61 (s), 32.98 (s), 33.60 (s), 37.56 (s), 39.26 (s), 44.15 (s), 45.95 (s), 114.88 (d), 119.45 (d), 123.14 (s), 126.76 (s), 128.98 (s), 130.69 (s), 136.17 (d), 141.83 (d), 143.46 (s), 158.29 (d) ppm

EXAMPLE 12

Preparation of trans-4-(trans-4-(2-(4-(4-fluorophenyl)phenyl)ethyl)cyclohexyl)-1-n-propyl-1-silacyclohexane 15.0 g of 4-(4-phenyl-4-n-propyl-4-silacyclohexyl)cyclohexane carbaldehyde was subjected to the Wittig reaction with a ylide compound obtained from 4-bromobenzyltriphenylphosphonium bromide to obtain 20.9 g (yield: 50%) of 4-(4-(2-(4-bromophenyl)ethenyl)cyclohexyl)-1-phenyl-1-n-propyl- 1-silacyclohexane. The results of IR absorption analysis are shown below. IR (liquid film) $v_{max}$: 2920, 2850, 1485, 1115, 1070, 1010, 965, 800 cm$^{-1}$ 42 ml of a tetrahydrofuran solution of 1.0 mole of 4-fluorophenylzinc chloride was dropped in a mixture of 18.0 g of the thus obtained product and 500 mg of tetrakis(triphenylphosphine)palladium (0) and 100 ml of tetrahydrofuran, followed by agitation for 19 hours. The reaction mixture was charged into an ammonium chloride aqueous solution and extracted with ethyl acetate. The ethyl acetate phase or solution was washed with brine, dried and concentrated, followed by purification through column chromatography to obtain 16.2 g (yield: 71%) of 4-(4-(2-(4-(4-fluorophenyl)phenyl)ethenyl)cyclohexyl)- 1-n-propyl-1-silacyclohexane. The results of IR analysis are shown below.

IR (liquid film) $v_{max}$: 2920, 2850, 1600, 1495, 1235, 1110, 805 cm$^{-1}$ 15.0 g of the thus obtained product was hydrogenated in the same manner as in Example 4 to obtain 14.8 g (yield: 98%) of 4-(4-(2-(4-( 4-fluorophenyl)phenyl)ethyl)cyclohexyl)-1-n-propyl-1-silacyclohexane. The results of IR analysis are shown below.

IR (liquid film) $v_{max}$: 2920, 2850, 1600, 1495, 1235, 1115, 815 cm$^{-1}$ 10.0 g of the thus obtained product was subjected to de-silylation reaction with iodine monochloride and then reduction with lithium aluminium hydride in the same manner as in Example 4 to obtain 5.2 g (yield: 61%) of the intended product. The results of IR and NMR analyses are shown below.

IR (KBr, disc) $v_{max}$: 2918, 2852, 2102, 1498, 1225, 1221, 1161, 889, 843, 820 cm$^{-1}$ $^{13}$C-NMR (CDCl$_3$): 10.12 (s), 14.79 (s), 17.80 (s), 17.94 (s), 28.60 (s), 29.62 (s), 32.94 (s), 33.61 (s), 37.59 (s), 39.33 (s), 44.16 (s), 45.96 (s), 115.50 (d), 126.84 (s), 128.45 (d), 128.79 (s), 137.28 (d), 137.50 (s), 142.40 (s), 162.26 (d) ppm

EXAMPLE 13

Preparation of trans-4-(trans-4-(2-(4-(3,4-difluorophenyl)phenyl)ethyl)cyclohexyl)-1-n-propyl-1-silacyclohexane The general procedure of Example 12 was repeated using 3,4-difluorophenylzinc chloride, thereby obtaining the intended product. The results of IR and NMR analyses are shown below.

IR (KBr, disc) $v_{max}$: 2916, 2850, 2104, 1506, 1402, 1309, 1279, 1182, 1065, 982, 889, 843, 810 cm$^{-1}$ $^{13}$C-NMR (CDCl$_3$): 10.13 (s), 14.79 (s), 17.80 (s), 17.94 (s), 28.60 (s), 28.61 (s), 32.96 (s), 33.60 (s), 37.58 (s), 39.28 (s), 44.16 (s), 45.96 (s), 115.72 (d), 117.37 (d), 122.71 (dd), 126.76 (s), 128.91 (s), 136.38 (s), 138.30 (dd), 143.05 (s), 148.25 (dd),. 151.90 (dd) ppm As will be apparent from the foregoing examples, the cyclohexane carbaldehyde compounds of the invention are useful intermediates for preparing liquid crystal compounds and can thus be used to derive various types of silacyclohexane-based liquid crystal compounds therefrom.

What is claimed is:

1. A cyclohexane carbaldehyde compound of the following formula (I)

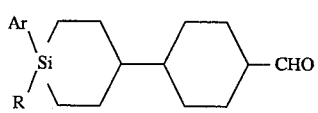

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms.

2. A process for preparing a silacyclohexane-based liquid crystal compound which comprises:

subjecting a cyclohexane carbaldehyde of the following general formula (I)

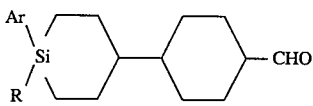

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, with a ylide compound of the following general formula

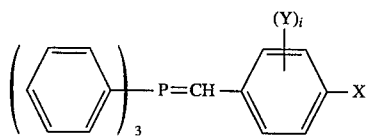

wherein X represents R or OR, in which R has the same meaning as defined above, CN, F, Cl, Br, CF$_3$, OCF$_3$, OCHF$_2$, OCHFCl, OCF$_2$Cl, CF$_2$Cl, (O)$_m$CY$_1$=CX$_1$X$_2$, or O(CH$_2$)$_r$(CF$_2$)$_s$X$_3$ wherein m is a value of 0 or 1, Y$_1$ and X$_1$ independently represent H, F or Cl, X$_2$ represents F or Cl, r and s are, respectively, a value of 0, 1 or 2 provided that r+s=2, 3 or 4, and X$_3$ represents H, F or Cl, Y represents a halogen or a methyl group, and i is a value of 0, 1 or 2, thereby obtaining a compound of the following formula

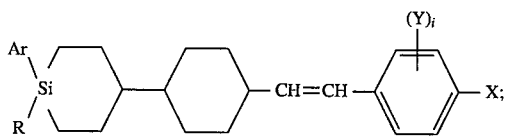

subjecting the thus obtained compound to hydrogenation to obtain a compound of the following general formula

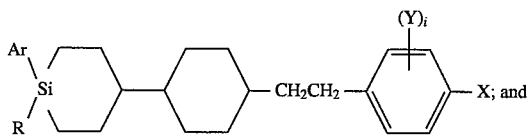

further subjecting the thus obtained compound to desilylation and then to reduction to obtain a silacyclohexane-based liquid crystal compound of the following general formula (II)

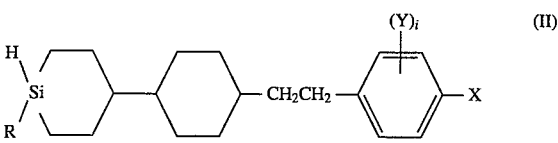

wherein R, X, Y and L have, respectively, the same meanings as defined above.

3. A process according to claim 2, wherein said desilylation is effected by reaction with an electrophilic reagent.

4. A process according to claim 3, wherein said desilylation is effected after addition of a Lewis acid or under irradiation of actinic light.

5. A process according to claim 2, wherein the reduction is effected by addition of a member selected from the group consisting of metal hydrides, complex hydrides and substituted hydrides thereof.

6. A process for preparing a silacyclohexane-based liquid crystal compound which comprises:

subjecting a cyclohexane carbaldehyde of the following general formula (I)

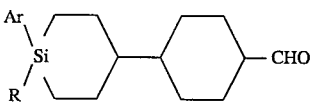

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, to reaction with a ylide compound of the following general formula

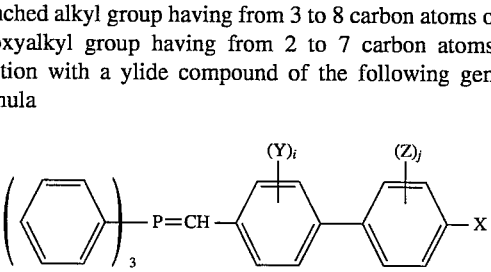

wherein X represents R or OR, in which R has the same meaning as defined before, CN, F, Cl, Br, CF$_3$, OCF$_3$, OCHF$_2$, OCHFCl, OCF$_2$Cl, CF$_2$Cl, (O)$_m$CY$_1$=CX$_1$X$_2$, or O(CH$_2$)$_r$(CF$_2$)$_s$X$_3$ wherein m is a value of 0 or 1, Y$_1$ and X$_1$ independently represent H, F or Cl, X$_2$ represents F or Cl, r and s are, respectively, a value of 0, 1 or 2 provided that r+s=2, 3 or 4, and X$_3$ represents H, F or Cl, Y and Z independently represent a halogen or a methyl group, i and j are independently a value of 0, 1 or 2, thereby obtaining a compound of the following general formula

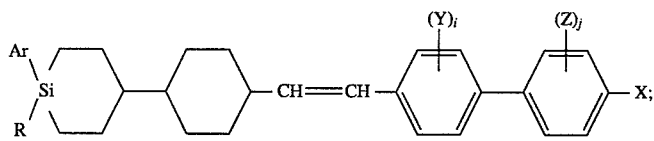

subjecting the compound of the above formula to hydrogenation to obtain a compound of the following general formula

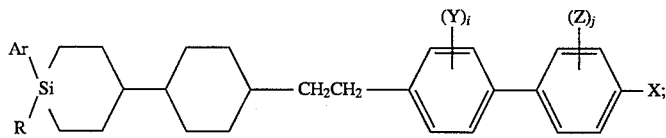

further subjecting the thus obtained compound of the above formula to de-silylation and then to reduction to obtain a silacyclohexane-based liquid crystal compound of the general formula (III)

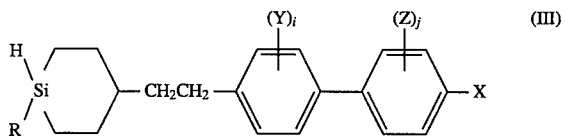

7. A process according to claim 6, wherein said de-silylation is effected by reaction with an electrophilic reagent.

8. A process according to claim 7, wherein said de-silylation is effected after addition of a Lewis acid or under irradiation of actinic light.

9. A process according to claim 6, wherein the reduction is effected by addition of a member selected from the group consisting of metal hydrides, complex hydrides and substituted hydrides thereof.

10. A process for preparing a silacyclohexane-based liquid crystal compound which comprises:

reacting a cyclohexane carbaldehyde of the following general formula (I)

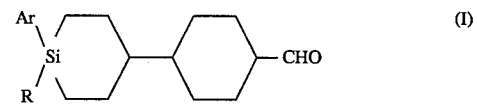

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, with a ylide compound of the following general formula

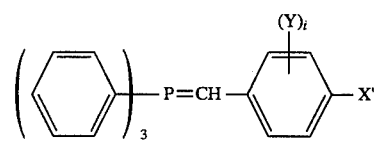

wherein X' represents a halogen, Y represents a halogen or a methyl group, and i is a value of 0, 1 or 2, thereby obtaining a compound of the following general formula Ar\
 \
  Si—⟨cyclohexane⟩—⟨cyclohexane⟩—CH=CH—⟨phenyl (Y)$_i$⟩—X';
 /
R/ further subjecting the compound of the above formula to reaction with an organometal compound of the following general formula in the presence of a catalyst of a transition metal compound $$M-\text{⟨phenyl }(Z)_j\text{⟩}-X$$

wherein X represents R or OR, in which R has the same meaning as defined before, CN, F, Cl, Br, $CF_3$, $OCF_3$, $OCHF_2$, $OCHFCl$, $OCF_2Cl$, $CF_2Cl$, $(O)_mCY_1=CX_1X_2$, or $O(CH_2)_r(CF_2)_sX_3$ wherein m is a value of 0 or 1, $Y_1$ and $X_1$ independently represent H, F or Cl, $X_2$ represents F or Cl, r and s are, respectively, a value of 0, 1 or 2 provided that r+s=2, 3 or 4, and $X_3$ represents H, F or Cl, M represents MgU or ZnU wherein U represents a halogen, $TiU_k(OW)_{3-k}$ wherein U has the same meaning as defined above, W represents an alkyl group and k is a value of 0, 1, 2 or 3, or B(OV) wherein V represents a hydrogen atom or an alkyl group, Z represents a halogen or $CH_3$ and i is a value of 0, 1 or 2, thereby obtaining a compound of the following general formula

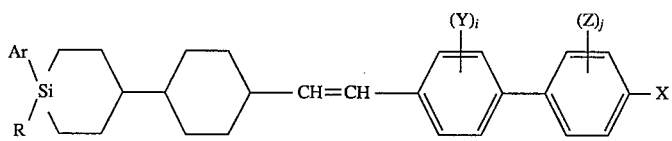

subjecting the compound of the above formula to hydrogenation, thereby obtaining a compound of the following general formula

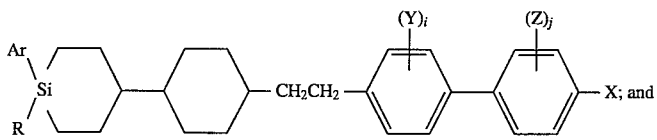

subjecting the compound of the above formula to desilylation and then to reduction to obtain a silacyclohexane-based liquid crystal compound of the following general formula (III)

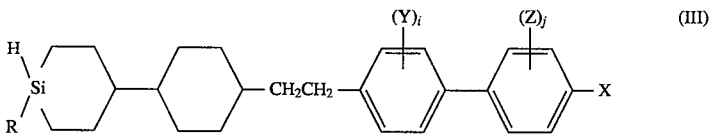

11. A process according to claim 10, wherein said desilylation is effected by reaction with an electrophilic reagent.

12. A process according to claim 11, wherein said desilylation is effected after addition of a Lewis acid or under irradiation of actinic light.

13. A process according to claim 10, wherein the reduction is effected by addition of a member selected from the group consisting of metal hydrides, complex hydrides and substituted hydrides thereof.

14. A process according to claim 10, wherein M representing said organometal compound is $B(OV)_2$ wherein V is H or an alkyl group, whereupon the reaction is effected under basic conditions.

* * * * *